United States Patent [19]

Vadher

[11] Patent Number: 4,946,446
[45] Date of Patent: Aug. 7, 1990

[54] RETRACTABLE NEEDLE

[76] Inventor: Dinesh L. Vadher, St. John's Medical Arts Bldg.-Rte. 25A, Smithtown, N.Y. 11787

[21] Appl. No.: 365,800

[22] Filed: Jun. 14, 1989

[51] Int. Cl.⁵ .............................................. A61M 5/32
[52] U.S. Cl. ................................... 604/198; 604/263; 604/205
[58] Field of Search ............... 604/197, 198, 187, 171, 604/263, 413, 205

[56] References Cited

U.S. PATENT DOCUMENTS

| | | |
|---|---|---|
| 4,194,505 | 3/1980 | Schmitz . |
| 4,425,120 | 1/1984 | Sampson et al. .......... 604/198 |
| 4,507,117 | 3/1985 | Uining et al. . |
| 4,664,654 | 5/1987 | Strauss . |
| 4,702,738 | 10/1987 | Spencer ...................... 604/198 |
| 4,747,831 | 5/1988 | Kolli . |
| 4,767,413 | 8/1988 | Haber et al. . |
| 4,772,272 | 9/1988 | McFarland . |
| 4,840,619 | 6/1989 | Hughes ........................ 604/198 |

Primary Examiner—Stephen C. Pellegrino
Attorney, Agent, or Firm—Leonard Belkin

[57] ABSTRACT

Safety hypodermic needle apparatus for disposing of a needle safely after use. The apparatus comprises a housing containing a plunger on which is mounted a needle at one end and an adapter at the other end for engaging a syringe. When the syringe is engaged and is used to push the plunger, the needle is positioned to extend from the housing ready for use. When the syringe is pushed once again after use, this causes the needle to be retracted. In another embodiment, an adapter is employed to permit the use of an evacuated tube for the collection of blood.

9 Claims, 3 Drawing Sheets

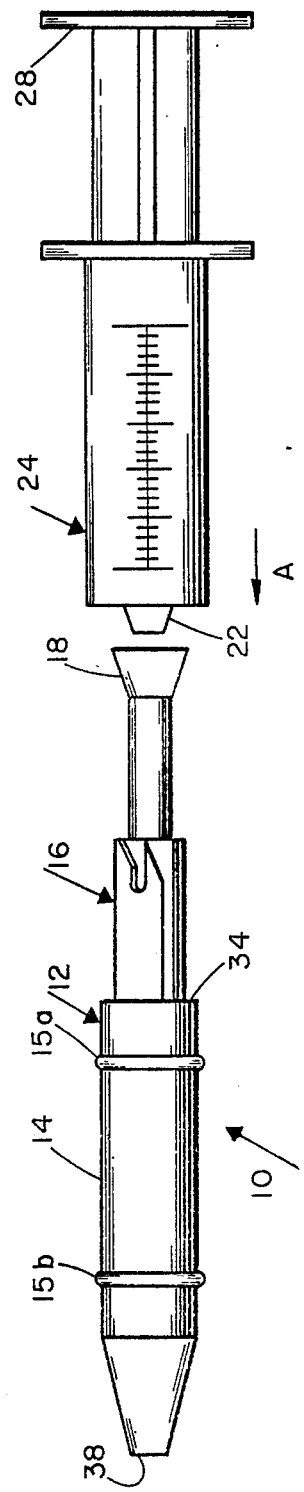
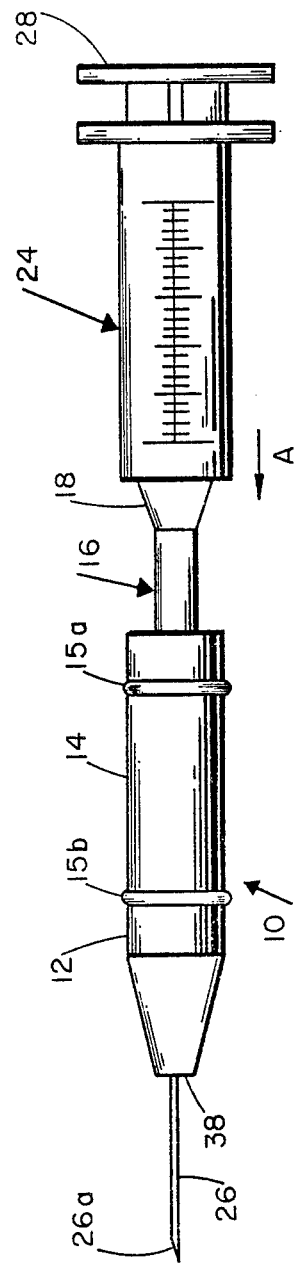

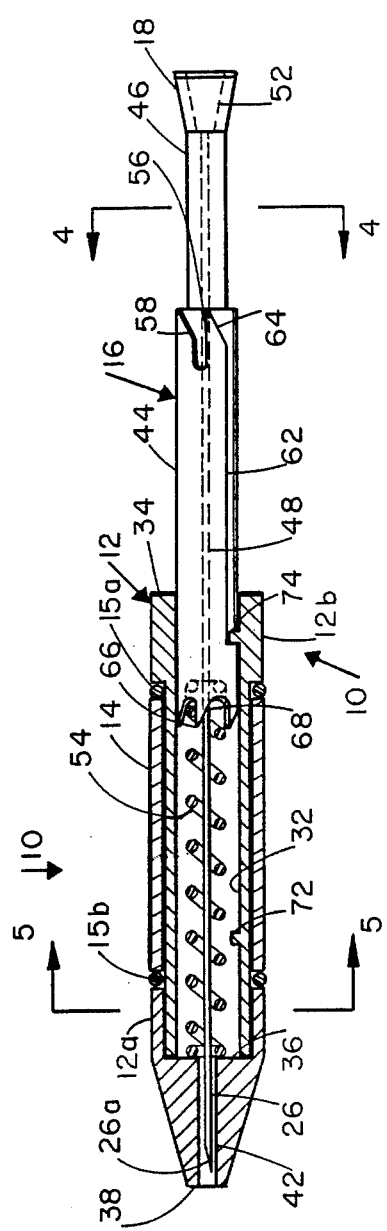
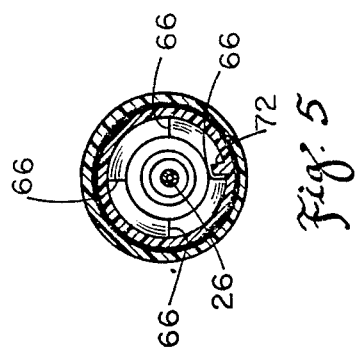
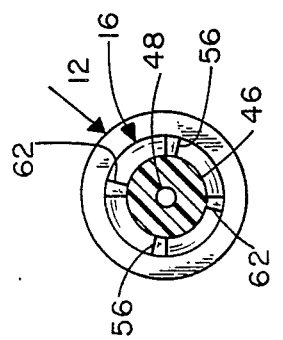

RETRACTABLE NEEDLE

BACKGROUND OF THE INVENTION

The present invention relates to apparatus for the safe disposal of hypodermic needles and more particularly to apparatus which will safely sheath a needle after use to avoid accidental puncture by a worker.

When a needle is inserted into a patient for the intravenous delivery of a fluid, or for the withdrawal of a blood sample, for example, the needle is withdrawn after use and dropped into a container for disposal.

The used needle is tipped with blood and represents a hazard for medical personnel. The blood may carry a communicable disease and there is always the danger of an accidental puncture. With the present concern over the transmission of AIDS and other serious diseases through the blood, there is interest in finding alternative and safer ways of disposing of such needles.

The following U.S. Pats. show a variety of arrangements designed to provide for the safe disposal of needles: 4,194,505, 4,507,117, 4,664,654, 4,747,831, 4,767,413, and 4,772,272. None of the preceding patents teaches the present invention.

SUMMARY OF THE INVENTION

In this invention there is provided disposable apparatus of simple and economic construction capable of sheathing for disposal of a used needle requiring little active intervention by the medical worker thereby virtually insuring that the used needle will be safely secured for disposal.

In accordance with a preferred embodiment of this invention there is provided a device in which a simple push extends the needle from one end for use and a successive push causes the needle to be retracted into the device. The other end of the device is provided with an adaptor for engagement with a syringe. For use with an evacuated tube for the withdrawal of blood, there may be provided means to penetrate said tube.

It is thus a principal object of this invention to provide improved apparatus for the safe disposal of a hypodermic needle.

Other objects and advantages of this invention will hereinafter become obvious from the following detailed description of preferred embodiments of this invention.

BRIEF DESCRIPTION OF THE DRAWINGS

FIG. 1 is an elevation view of a safety hypodermic needle incorporating the principles of this invention with the needle retracted and about to be engaged by a syringe.

FIG. 2 is a view similar to FIG. 1 with the syringe attached and the needle extended for use.

FIG. 3 is a view similar to FIG. 1 in partial section.

FIGS. 4 and 5 are views along 4—4 and 5—5 of FIG. 3.

DETAILED DESCRIPTION OF THE PREFERRED EMBODIMENTS

Figure 6:
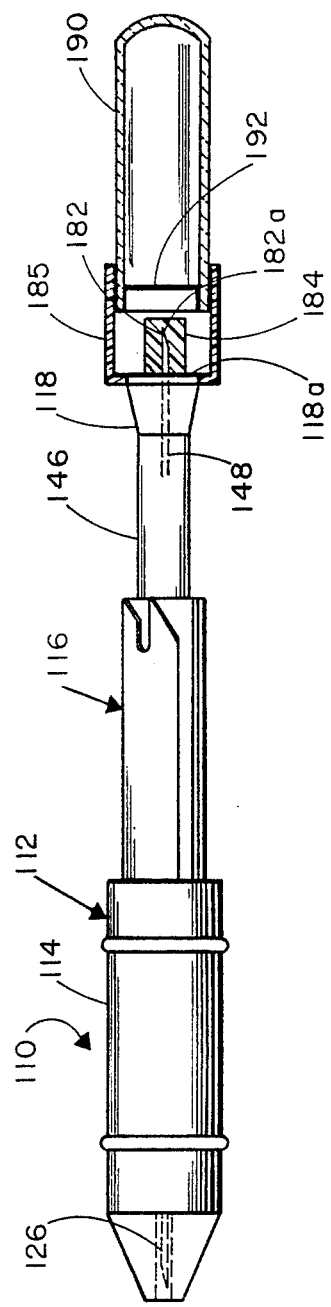
FIG. 6 is a view similar to FIG. 1 showing an alternative embodiment of this invention.

Referring to FIGS. 1 and 2, safety hypodermic needle device 10 consists of a housing 12 with a freely rotating sleeve 14 and a plunger 16 having a tapered adapter 18 at its back or proximate end to engage nozzle 22 of syringe 24. As seen in FIG. 1, needle device 10 is retracted and syringe 24 is about to engage plunger 16 at adapter 18.

Sleeve 14 is cylindrical and is free to rotate. A pair of rings 15a and 15b at opposite ends of sleeve 14 made of an anti-friction material such as Teflon facilitates this.

When syringe 24 engages adapter 18 as shown in FIG. 2, syringe 24 is employed to push plunger 16 to the left as shown by arrow A, causing needle 26 to extend out from the front or distal end of device 10 and is ready to be employed.

When syringe 24 is emptied as shown in FIG. 2 with piston 28 fully depressed, syringe 24 is pushed once again to the left which results in plunger 16 returning to its position shown in FIG. 1, sheathing needle 26 so that it is no longer capable of causing any harm, and the complete assembly of device 10 and syringe 24 may be disposed of together or separately.

For the details of construction of safety hypodermic needle device 10, reference is made to FIGS. 3, 4, and 5. Housing 12 is hollow made of two parts 12a and 12b rigidly attached to each other having a cylindrical opening or interior 32 extending to proximate end 34 and terminating in a wall or shoulder 36 near its distal end 38 which is conical in configuration as illustrated. An opening 42 provides communication between interior 32 and end or tip 38 of housing 12.

Plunger 16 extending into interior 32 of housing 12 consists of a solid cylindrical member 44 with an extension 46 of reduced diameter extending out and terminating in adapter 18 which as shown in FIGS. 1 and 2 communicates with syringe 24. Referring back to FIGS. 3, 4, and 5, plunger 16 is provided with a passageway 48 which terminates in adapter 18 with a flared opening 52 to mate with nozzle 22 of syringe 24.

Passageway 48 extends the full length of member 44 where one end of needle 26 is mounted as illustrated. Hence, when syringe 24 is engaged with plunger 16 as illustrated in FIG. 2, there is communication between the interior of syringe 24 and needle 26 which is hollow as is understood in the art.

A coil spring 54 circling needle 26 is mounted within interior 32 between shoulder 36 and the interior end of plunger 16, nesting within the latter as shown, biasing plunger 16 to the right at all times. When plunger 16 is in its retracted position as shown in FIGS. 1 and 3, needle 26 is retracted and located completely and securely within housing 12. When plunger 16 is in its depressed position as shown in FIG. 2, tip 26a of needle 26 is exposed and ready for use.

In order to effect the movement of plunger 16 in accordance with the principles of this invention, member 44 is provided at its right or proximal end with a pair of short grooves 56 which are 180 deg. apart from each other, each provided with one sloping side 58 and a pair of long grooves 62 each with a sloping side 64 located 180 deg. apart from each other and offset 90 deg. from short grooves 56.

The other or distal end of plunger 16 is provided along its outer periphery with four saw-like teeth 66 each having a sloping side 68. Teeth 66 are located 45 deg. apart from each other with the exposed point of each tooth aligned with either groove 56 or 62. A cam operator 72 in the shape of a pin is mounted on the inner wall of interior 32 to engage with the sloping sides 68 of teeth 66 so that each time plunger 16 is pushed toward the conical end 38 of device 10, plunger 16 is caused to rotate 45 deg.

Interior 32 of housing 12 is provided with a second cam operator 74 which may also be in the form of a pin to fall into the bottom of either slot 56 or slot 62. When cam operator 74 is in the bottom of slot 62, then needle 26 is retracted as shown in FIG. 3. When cam operator 74 is in the bottom of slot 56, then plunger 16 would be in the position shown in FIG. 2, with needle 26 extended out and ready for use. Each time plunger 16 is pushed to the left it is rotated into the next position, alternating between the two positions just described with cam operator 74 in either slot 56 or 62.

In the operation of the apparatus just described, safety hypodermic needle device 10 is available and shipped with the needle retracted as shown in FIG. 1, sterilized and packaged, ready for use. A similarly sterilized and packaged syringe 24 is available for use. If syringe 24 is to be employed to inject a medicamant into a patient, syringe 24 is filled to the correct volume of the pharmaceutical with the result that piston 28 is retracted as shown in FIG. 1. Syringe 24 is engaged with device 10 by inserting nozzle 22 into opening 52 of adapter 18.

While grasping freely rotating sleeve 14 with the fingers of one hand, and holding the barrel of syringe 24 with the other hand, the latter is pushed to the left as shown in FIG. 2 causing plunger 16 to move to the left depressing spring 54, causing housing 12 to be rotated by cam operator 72, and having cam operator 74 to drop into slot 56 whereby the tip 26a of needle 26 becomes exposed for use as seen in FIG. 2. By grasping sleeve 14 which is freely rotating, it is seen that the worker need not rotate either hand because housing 12 will rotate within sleeve 14. Hence, it is understood that when plunger 16 is described herein as rotating with respect to housing means 12 it is understood that this includes plunger 16 remaining stationary and housing 12 being rotated.

The medical worker can then insert needle 26 in the patient, and make the injection by pushing piston 28 in to the left causing the medication to pass through passageway 48 and needle 26. After the injection is completed, syringe 24 is pushed once more to the left to cause cam operator 74 to land in slot 62 leaving needle 26 retracted and sheathed as shown in FIG. 3.

The whole assembly consisting of device 10 connected to syringe 24 may be disposed of together.

In the event syringe 24 is to be used to draw blood, empty syringe 24 would be connected with piston 28 in its depressed position, so that after plunger 16 is depressed to expose needle 26 and the puncture is made, withdrawal of piston 28 will result in blood being drawn into the body of syringe 24.

If blood is to be drawn from the patient using an evacuated sealed test tube as is now quite frequently used, then a slightly different design of device would be employed. Referring to FIG. 6, there is illustrated safety hypodermic needle device 110 identical to device 10 shown in FIGS. 1-5 except that extension 146 from plunger 116 is provided with an adapter 118 having passageway 148 extending without flaring to end 118a of adapter 118. Shown are needle 126, rotatable sleeve 114 and housing 112. Inserted in passageway 148 and extending out therefrom is a hollow needle 182 having a sharp edge 182a and encased in a rubber sleeve 184 for a purpose to be described. Mounted on adapter 118 is a cylindrical shield 185 to prevent accidental contact with needle 182.

For use with device 110 there is evacuated test tube 190 plugged at its open end with a suitable rubber cork 192 designed to maintain the vacuum within tube 190. As is understood in the art, cork 192 is made of material which is capable of being penetrated by a needle, such as needle 182 just described.

In using device 110, plunger 116 is pushed in by grasping the barrel of plunger 116 so that needle 126 is extended as in FIG. 2, and the needle inserted into a patient for the taking of blood. Test tube 190 would then be pushed up against transition 118 so that needle 182 penetrates its sleeve 184 and cork 192 completely through so that the vacuum within tube 190 will withdraw the blood without further action on the part of the medical worker. Test tube 190 would then be separated from needle 182 and device 110 disposed of by first retracting needle 126 as previously described.

It will be seen that the invention as herein described makes it possible to have a device which requires very little if any special procedures which will result in the safe disposal of used needles. In addition, the embodiments disclosed are simple and economic in construction so that they can readily be made disposable at very little additional cost.

While only certain preferred embodiments of this invention have been described it is understood that many variations of this invention are possible without departing from the principles of this invention as defined in the claims which follow.

What is claimed is:

1. Apparatus for the safe disposal of a needle which is part of said apparatus comprising:
    a. extended housing means having an opening at the distal end for accomodating said needle and an opening at its proximate end;
    b. plunger means mounted and being both slidable and rotatable within said housing means and extending out of the proximate end of said housing means;
    c. a passage extending through said plunger means;
    d. said needle having one end mounted within said passageway and extending out of said plunger means in the direction of the distal end of said housing means;
    e. means within said housing means for biasing said plunger means toward the proximate end of said housing means;
    f. cam and slot means on said plunger means, and cam operating means mounted on the inside of said housing means for cooperating with said cam and slot means to establish a number of discrete positions of said plunger means, including a first axial position along the length of said housing means with said needle extending out of the distal end of said housing means with said needle retracted into said housing means;
    g. said discrete positions of said plunger means including a plurality of positions as said plunger means is rotated so that said plunger means may be positioned both axially and rotationally;
    h. said passageway including means adjacent the end of said plunger means extending from the proximate end of said housing means having means for engaging a syringe; and
    i. said cam and slot means including means upon said plunger means being pushed toward the distal end of said housing means for overcoming said biasing means for rotating said plunger means into the next successive radial position and placing said plunger means into its next successive axial position along the length of said housing means, said biasing means locking said plunger means in each next successively position, so that in successive pushes of said plunger means said needle alternates between extending out from said housing means and being retracted into said housing means.

2. The apparatus of claim 1 wherein said cam and slot means comprises a plurality of circumferentially arranged axially extending slots on said plunger means adjacent the proximate end thereof whose depths alternate to correspond to the first and second axial positions of said plunger means, said cam operating means including first pin means for falling into a slot to establish the axial position of said plunger means.

3. The apparatus of claim 2 wherein said cam and slot means includes a plurality of cam surfaces circumferentially arranged along the distal end of said plunger means, said cam operating means including second pin means mounted in said housing means for making contact with one of said cam surfaces when said plunger means is pushed to cause the rotation of said plunger means.

4. The apparatus of claim 1 wherein said housing means includes a rotatable sleeve for grasping said housing means so as to permit said housing means to rotate with respect to said plunger means while said sleeve remains stationary.

5. Apparatus for the safe disposal of a hollow needle which is part of said apparatus comprising:
 a. housing means and means within said housing means to support said needle;
 b. said support means being axially movable between a first axial position in which said needle is extended for use and a second axial position in which said needle is entirely within said housing means;
 c. said support means being rotatable and having discrete radial positions in which said support means alternates between said first and second axial positions as said support means moves from one radial position to the next radial position;
 d. means mounted in said housing means acting in response to the pushing of said support means in one direction for moving said support means from one of said axial positions to the other of said axial positions whereby said needle is extended for use or sheathed within said housing means depending on which axial position said support means is located; and
 e. means within said support means for communicating with the interior of said needle to permit use of said needle when extended for use.

6. The apparatus of claim 5 in which said needle is attached to and extends from the distal end of said support means and said communicating means includes a passageway extending the full length of said support means to the proximate end thereof where such communication may be made.

7. The apparatus of claim 6 wherein the proximate end of said support means includes means for engaging a syringe.

8. The apparatus of claim 6 wherein the proximate end of said support means includes means comprising a needle to penetrate a tube having a vacuum for withdrawing blood.

9. The apparatus of claim 7 wherein said housing means includes stationary holding means permitting said housing means to rotate with respect to said support means as said support means is pushed to change position of said needle.

* * * * *